United States Patent [19]

Houswerth

[11] Patent Number: 5,135,471
[45] Date of Patent: Aug. 4, 1992

[54] CRUCIFORM ANTERIOR SPINAL HYPEREXTENSION ORTHOSIS

[75] Inventor: John R. Houswerth, Bourbonnais, Ill.
[73] Assignee: R.A. Storrs, Inc., Kankakee, Ill.
[21] Appl. No.: 756,352
[22] Filed: Sep. 9, 1991
[51] Int. Cl.$^5$ ............................................. A61F 5/02
[52] U.S. Cl. .................................. 602/19; 128/102.1; 128/106.1; 128/108.1
[58] Field of Search .................... 128/78, 95.1, 96.1, 128/99.1, 106.1, 108.1, DIG. 19, 102.1; 602/19

[56] References Cited

U.S. PATENT DOCUMENTS

| | | |
|---|---|---|
| Re. 31,564 | 4/1984 | Hendricks . |
| 1,948,785 | 2/1934 | Dondelinger .................... 128/108.1 |
| 1,981,157 | 11/1934 | Walter ................... 128/99.1 |
| 2,523,232 | 9/1950 | Portnow ............................ 128/95.1 |
| 4,640,269 | 2/1987 | Goins . |
| 4,976,257 | 12/1990 | Akin et al. . |

OTHER PUBLICATIONS

Orthopedic Appliance Atlas, vol. 1; American Academy of Orthopedic Surgeons, p. 183, 1952.

Primary Examiner—Richard J. Apley
Assistant Examiner—Linda C. M. Dvorak
Attorney, Agent, or Firm—Anthony S. Zummer

[57] ABSTRACT

A cruciform anterior spinal hyperextension orthosis has a rigid cruciform base. The base includes an elongated upright and a crossarm secured to the upright. The crossarm has a pair of oppositely extending ends with a side pad on each end. The upright has a upper end and an opposed lower end. A pubic pad is connected to the lower end of the upright. A pair of spaced apart pectoral pads is pivotally connected to the upper end of the upright.

8 Claims, 2 Drawing Sheets

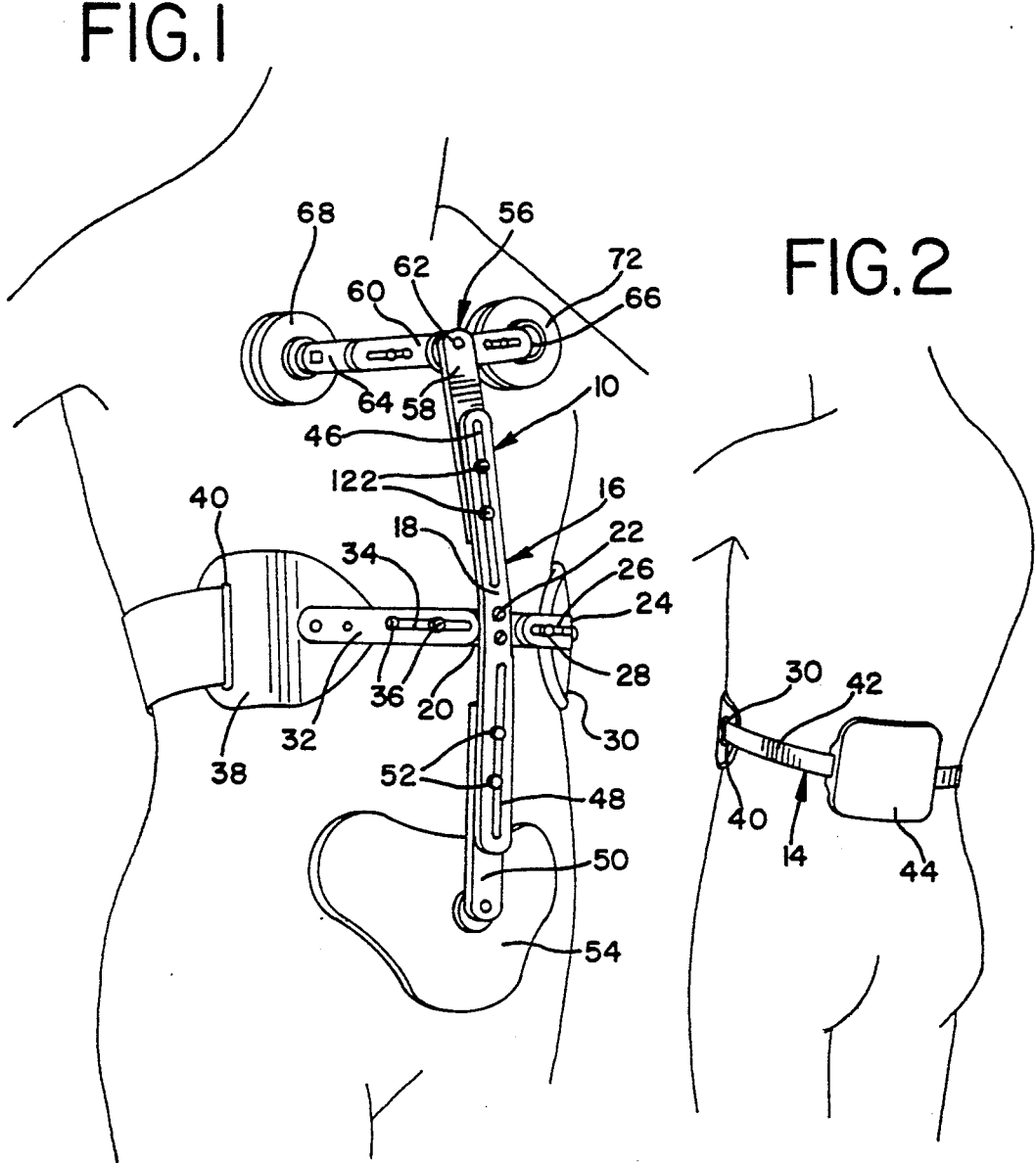
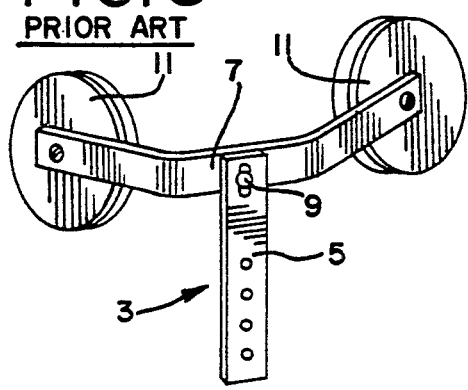

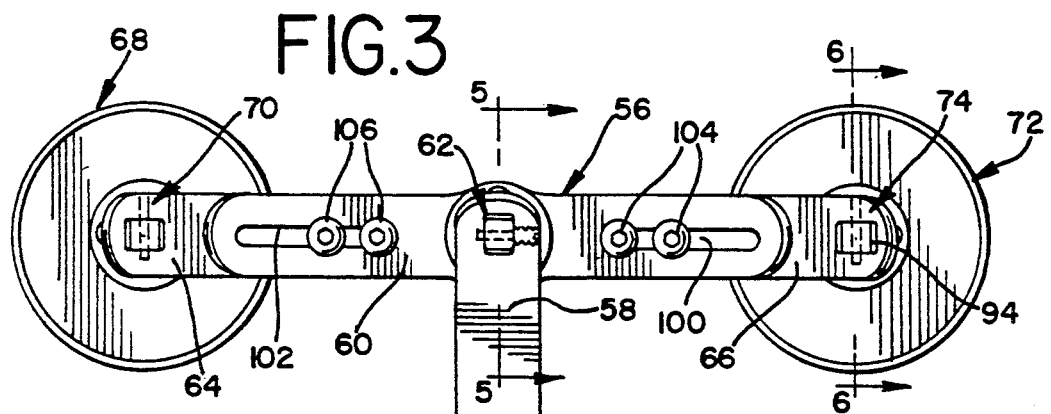
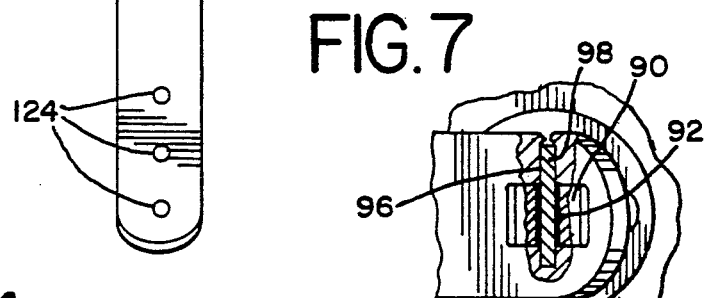
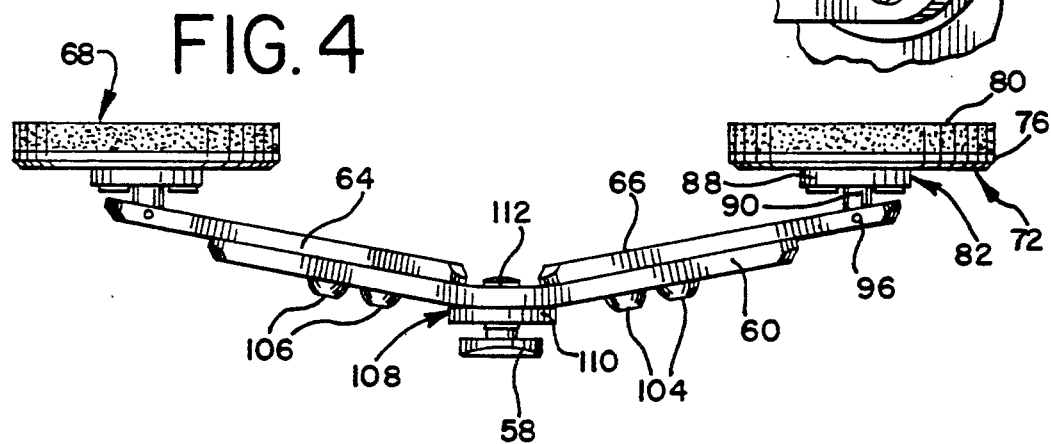
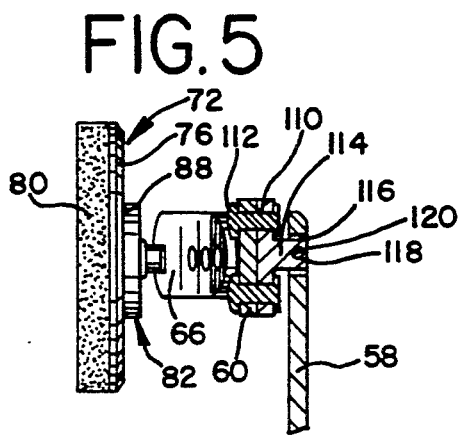
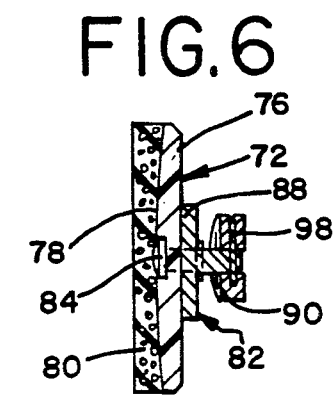

CRUCIFORM ANTERIOR SPINAL HYPEREXTENSION ORTHOSIS

BACKGROUND OF THE INVENTION

The use of a cruciform anterior spinal hyperextension orthosis is well known and widely accepted in the treatment of certain specific abnormalities of the spine. A cruciform orthosis, which has gained a wide degree of acceptance, is disclosed in U.S. Pat. No. 4,173,973 entitled, "Hyperextension Back Brace" issued Nov. 13, 1979 to David J. Hendricks. The patent was reissued as RE 31,564 on Apr. 24, 1984. A commercial embodiment of the cruciform orthosis, which is taught in the patent, is shown in a catalog sheet entitled, "The CASH Orthosis" published by Ralph Storrs, Inc. of 197 South West Avenue, Kankakee, Ill. The catalog sheet has a copyright date of 1985.

The known cruciform orthosis applies a force to the anterior of a patient's body and a balanced force to the posterior of the body and thus the spine. The force on the patient's anterior is generally applied by two pads. One pad is positioned in the patient's pubic area and the other is positioned on the sternum. The forces from the two pads on the patient's anterior are balanced by a back strap which is in engagement generally with the lumbar area of the posterior to apply a constant force to the spine. Some patients suffer some discomfort when they wear the known cruciform orthosis because the sternal pad rests on the sternum where there is very little muscle and fat to dissipate the load from the sternal pad.

The use of pectoral pads in a back brace is well known and accepted in the art. A Bigg back brace with pectoral pads is taught at page 183 of the *Orthopaedic Appliances Atlas*, Volume 1 published by J.W. Edwards of Ann Arbor, Mich., 1952. The Bigg back brace has two pectoral pads supported by an upright which is located on the posterior of the patient. The pectoral pads are supported by bars which curve around opposite sides of the patient's body, thus giving rise to "cowhorns" as an identification of the arrangement. The "cowhorns" arrangement is heavy and is uncomfortable for the patient.

In view of the undesirability of the "cowhorn" arrangement, a prior art T-support 3, such as that shown in FIG. 8, has been used in the prior art cruciform orthosis instead of a single sternal pad. T-support 3 has an upright 5 which is adapted to be connected to an upper vertical arm of the Hendricks cruciform orthosis in substitution for the movable arm part of the Hendricks device. A cross memmber 7 is pivotally connected to upright 5 by hinge 9. A conventional pectoral pad 11 is fixed on each of the opposite ends of crossmember 7 of the T-support. Though the use of the two pectoral pads provides a greater degree of comfort over a single sternal pad, the pectoral pads do not accommodate themselves to movement of the patient relative to the subject orthosis.

SUMMARY OF THE INVENTION

The present invention provides an improvement in the widely accepted Hendricks cruciform anterior spinal hyperextension orthosis, even when used with a T-support with a pair of pectoral pads. The instant cruciform orthosis has as part of its construction the well known organization of an elongated upright with an elongated crossarm secured to the upright. The crossarm includes a pair of outwardly extending ends with a side pad connected to and supported by each of the outwardly extending ends. A back strap is connected to the side pads and is adapted to engage the posterior of the patient, generally in the lumbar region. The upright has a pubic pad connected to its lower end. The improvement of the present cruciform orthosis includes an elongated pectoral base bar pivotally connected to the upper end of the upright by a bar hinge. The bar hinge has an axis of pivoting substantially perpendicular to the length of the upright, and the pectoral base bar is bowed and is generally parallel to the axis of pivoting. A pectoral pad bar is releasably connected to each of opposite ends of the pectoral base bar. Each of the pectoral pad bars is elongated and has one end connected to the pectoral base bar. A pectoral pad is pivotally connected to the other end of each of the pectoral base bars by a respective pectoral pad hinge. Each of the pectoral pad hinges has an axis of pivoting substantially parallel to the length of the upright.

BRIEF DESCRIPTION OF THE DRAWING

FIG. 1 is a partial anterior and partial side view of a patient wearing the subject cruciform anterior spinal hyperextension orthosis;

FIG. 2 is a partial posterior and partial side view showing a back strap and back pad on a patient wearing the herein disclosed orthosis which is also shown in FIG. 1;

FIG. 3 is a front elevational view of a pectoral pad assembly connected to a sternal bar of the instant orthosis shown in FIGS. 1 and 2;

FIG. 4 is a plane view of the portion of the orthosis shown in FIG. 3;

FIG. 5 is a cross sectional view taken on line 5—5 of FIG. 3;

FIG. 6 is a cross sectional view taken on line 6—6 of FIG. 3;

FIG. 7 is an enlarged fragmentary portion of a hinge connection of a pectoral pad of FIG. 3 to a pad bar with a portion of the pad bar broken away to show a hinge pin; and FIG. 8 is a perspective view of a prior art T-support with a pair of pads mounted thereon, which T-support is adapted to be a part of a known cruciform orthosis.

DESCRIPTION OF THE PREFERRED EMBODIMENT

Referring now to the drawings and especially FIGS. 1 and 2, a cruciform anterior spinal hyperextension orthosis being a specific embodiment of the present invention is shown therein and is generally indicated by numeral 10. The cruciform orthosis generally consists of a substantially rigid anterior brace assembly 12 and a back strap and pad assembly 14 attached to brace assembly 12. As may be seen in FIG. 1, brace assembly 12 is mounted on the anterior of the patient's body while the back strap is connected to the brace assembly and wraps around the patient's body to engage the lumbar region of the patient's posterior.

The brace assembly generally includes a cruciform base 16. The cruciform base includes a bowed elongated metal upright 18 and a bowed metal crossarm 20 fixed to the upright by two conventional fasteners 22. The bows of the upright and the crossarm have the respective concave portions adjacent to a patient's body as is described in detail hereinafter.

A right lateral arm 24 is connected to one end of the crossarm as may be seen in FIG. 1. The right lateral arm includes a slot 26. A pair of conventional screws 28 is mounted in slot 26. Screws 28 are threadedly mounted in the crossarm. Screws 28 may be loosened so that the right lateral arm may be adjusted along the crossarm. The screws are tightened when arm 24 is properly positioned to lock the arm to the crossarm. A side pad 30 is connected to the right lateral arm. A left lateral arm 32 has a slot 34 which receives conventional screws 36. Screws 36 are threadedly mounted in the crossarm for adjustably positioning the left lateral arm along the crossarm in the same manner that the right lateral arm is adjustably locked to the crossarm. A side pad 38 is mounted on the left lateral arm. Side pads 30 and 38 have the same construction, to wit, a stiff polyethylene face plate with a conforming resilient foam padding mounted on the face plate. Each of the side pads 30 and 38 has a strap slot 40 which receives a conventional back strap 42 for going around to the posterior of the patient. A back pad 44 is mounted on back strap 42 for engagement with the patient's posterior.

Upright 18 has an upper slot 46 which extends toward its upper end and a lower slot 48 which extends toward its lower end. A pubic bar 50 has a pair of conventional screws 52 threadedly mounted therein. Screws 52 are mounted in slot 48 so that the pubic bar 50 may be selectively positioned and locked relative to upright 18 in the same manner that the lateral arms are locked to the crossarm. A conventional pubic pad 54 is mounted on the end of pubic bar 50. The pubic pad construction, which is well known, includes a stiff polyethylene outer face plate with a resilient foam padding on the face plate.

A pectoral pad support assembly 56 is mounted on the upper end of upright 18. The details of construction of the pectoral pad support assembly 56 are best seen in FIGS. 3 through 7. The pectoral pad support assembly includes a metal elongated sternal bar 58 with a metal bowed elongated pectoral base bar 60 connected to the sternal bar by a bar hinge 62. A metal elongated left pectoral pad bar 64 is connected to one terminal or end of base bar 60, and a metal elongated right pectoral pad bar 66 is connected to the opposite terminal or end of the base bar 60. Right pectoral pad bar 66 is a mirror image of left pectoral bar 64. A left pectoral pad 68 is pivotally connected to the left pectoral pad bar 64 through a pectoral pad hinge 70. A right pectoral pad 72 is pivotally connected to right pectoral pad bar 66 through pectoral pad hinge 74.

Pectoral pads 68 and 72 have the same construction. The construction of pad 72 may be best seen in FIGS. 3, 5 and 6. Pad 72 includes stiff polyethylene outer face plate 76. The face plate has a flat side to which is connected hinge 74. Inner surface 78 of face plate 76 is convex as may be best seen in FIG. 6. A conventional resilient foam padding 80 is secured to inner surface 78.

Hinge 74 includes pad support 82 secured to the flat side of face plate 76 by a pair of conventional fasteners 84. The pad support includes a circular foot 88 and an integral pedestal 90. The pedestal has a hinge pin aperture 92 extending therethrough, which aperture 92 is best seen in FIG. 7. Right pad bar 66 includes a pedestal aperture 94 for receiving pedestal 90. Pad bar 66 contains a pin receptacle opening 96. A hinge pin 98 is mounted in receptacle opening 96 and extends through hinge pin aperture 92 of the pedestal as is shown in FIG. 7. During assembly of the hinge, hinge pin 98 is positioned in pin receptacle opening 96 and hinge pin aperture 92, then the open end of receptacle opening 96 is swaged over to lock pin 98 into position, thereby completing hinge 74. Pin 98 is substantially perpendicular to the length of pad bar 66 and is thereby generally parallel to the length of upright 18 so that pectoral pad 72 pivots about an axis generally parallel to the upright.

Pad hinge 70 pivotally connects pad 68 to bar 64. The construction of hinge 70 is identical to the construction of hinge 74 described in detail above.

Base bar 60 includes a right slot 100 which extends toward the right end of the bar and a left slot 102 which extends toward the left end of the bar. Two screws 104 are threadedly mounted in pad bar 66. Screws 104 are positioned in slot 100 so that tightening of screws 104 releasably locks pad bar 66 relative to the base bar. Two screws 106 are threadedly mounted in left pad bar 64 and are positioned in slot 102. Screws 106 releasably lock the left pad bar relative to the base bar in the same manner that screws 104 releasably lock the right pad bar relative to the base bar.

Base bar hinge 62 pivotally connects the base bar to sternal bar 58. Base bar hinge 62 includes a bar support 108. The bar support 108 has a circular foot 110 which is fixed to the base bar by a pair of rivets 112. A pedestal 114 is formed integral with foot 110. The pedestal is positioned in a pedestal aperture 116 in sternal bar 58. Pedestal 114 includes a hinge pin aperture 118. The sternal bar has a hinge pin receptacle opening similar to pin receptacle opening 96. A hinge pin 120 is mounted in the sternal bar hinge pin receptacle opening and through aperture 118 in the pedestal in the same manner that hinge pin 98 is mounted in its opening 96 and aperture 92. After pin 120 is positioned in its opening and aperture 118, the opening in the sternal bar adjacent to the surface is swaged to close off the opening and lock pin 120 into position in the same manner that hinge pin 98 is locked into position. Hinge pin 120 is arranged substantially perpendicular to the length of sternal bar 58 so that the pectoral base bar is pivotal in an axis which is substantially perpendicular to the length of sternal pad and the upright.

Two screws 122 are threadedly mounted in selected apertures 124 in the sternal bar. Screws 122 are positioned in slot 46 of the upright so that the sternal bar may be selectively moved along the upper portion of the upright then releasably locked into position.

The subject cruciform orthosis is readily adjustable to insure a proper fit to a given patient. The spacing between the side pads is set by adjustment of the position of the lateral arms relative to the crossarm. The two lateral arms 24 and 32 are releasably locked to crossarm 20 by screws 28 and 36, respectively. The crossarm is bent slightly so that side pads 30 and 38 contact the patient but the crossarm does not engage the patient due to the curvature of the patient's thorax. Pubic pad 50 is positioned relative to the crossarm by loosening screws 52 to allow the pubic bar to move relative to the lower portion of upright 18 to a selected position. Screws 52 lock the pubic bar relative to the upright once the selected position is attained.

The pectoral pads 68 and 72 are positioned relative to pubic pad 54 by adjusting the sternal bar relative to the upright and then releasably locking the sternal bar relative to the upright by means of screws 122. The distance between pectoral pads 68 and 72 is adjusted to accommodate a given patient by appropriately positioning the pad bars relative to the base bar and releasably locking pad bars 64 and 66 to base bar 60 with screws 106 and 104, respectively. The base bar is bowed so that the pectoral pads contact the patient but there is no opportunity for the metal pad bars or sternal bar to engage the patient.

The patient comfort is enhanced by the present construction in view of the fact that there is a range of automatic adjustment of the pectoral pads as the patient moves. The base bar pivots relative to the upright about an axis which is perpendicular to the length of the upright. Each of the pectoral pads pivots relative to its respective pad bar and the upright about an axis which is parallel to the length of the upright. The effective pivoting of the pectoral pads about the respective two axis allows the pectoral pads to engage firmly the patient but still allows for adjustment of the pads as the patient moves to provide a greater degree of patient comfort. Furthermore, it is clear that the pectoral pads may be positioned to an area where there is a greater amount of muscle and fat to provide improved patient comfort rather than have a pad rest on the sternum.

A specific embodiment of the herein disclosed invention has been described in detail above. It is to be expressly understood that the detailed description of the specific embodiment including the use of specific material is disclosed herein in compliance with the applicable statues. Those skilled in the art may make various changes in materials and in the construction of a specific orthosis without departing from the spirit and scope of the present invention. It is to be expressly understood that the scope of the herein disclosed invention is limited only by the appended claims.

What is claimed is:

1. In a cruciform anterior spinal hyperextension orthosis having; a rigid cruciform base including an elongated upright and a crossarm secured to the upright, said crossarm having a pair of outwardly extending ends, said upright having an upper end and an opposed lower end, and a pubic pad connected to the lower end of the upright, the improvement comprising, a pair of pectoral pads pivotally connected to the upright, said pectoral pads being spaced apart from each other, each of said pectoral pads having an axis of pivoting substantially parallel to the upright.

2. In a cruciform anterior spinal hyperextension orthosis as defined in claim 1, including, a pectoral base bar pivotally connected to the upper end of the upright, and said base bar having a pair of oppositely spaced terminals, each of the terminals having one of the pectoral pads of the pair of spaced pectoral pads connected thereto.

3. In a cruciform anterior spinal hyperextension orthosis as defined in claim 1, including, a right pectoral pad bar pivotally connected to one of the pectoral pads, said right pectoral pad bar connected to the upright, and a left pectoral pad bar pivotally connected to the other of the pectoral pads, said left pectoral pad bar connected to the upright.

4. In a cruciform anterior spinal hyperextension orthosis as defined in claim 1, including, an elongated pectoral base bar connected to the upper end of the upright, said base bar being substantially perpendicular to the length of the upright, said base bar having a pair of oppositely spaced terminals, one of said pectoral pads mounted on each of the terminals, and a hinge connecting each of the pectoral pads to its respective terminal.

5. In a cruciform anterior spinal hyperextension orthosis as defined in claim 1, including, an elongated pectoral base bar pivotally connected to the upper end of the upright, said base bar having a pair of oppositely spaced terminals, a right pectoral pad bar connected to one of the oppositely spaced terminals, one of the pectoral pads pivotally mounted on the right pectoral pad bar, and a left pectoral pad bar mounted on the other of the pair of oppositely spaced terminals, the other pectoral pad pivotally mounted on the left pectoral pad bar.

6. In a cruciform anterior spinal hyperextension orthosis as defined in claim 1, including, an elongated pectoral base bar connected to the upper end of the upright, said base bar having a pair of oppositely spaced terminals, and a pectoral pad hinge connected to each of the terminals, each hinge having one of the pectoral pads mounted thereon to allow each of the pectoral pads to pivot relative to the pectoral base bar.

7. In a cruciform anterior spinal hyperextension orthosis as defined in claim 1, including, a pectoral pad bar connected to each of the pectoral pads, each of the pectoral pad bars connected to the upright, and a hinge connecting each pectoral pad with its respective pectoral pad bar to allow each pectoral pad to pivot relative to its respective pectoral pad bar.

8. In a cruciform anterior spinal hyperextension orthosis having, a bowed elongated upright, a bowed elongated crossarm secured to the upright, said crossarm having a pair of outwardly extending ends, a side pad connected to each of the outwardly extending ends, a back strap connected to the side pads, said upright having an upper end and an opposite lower end, a pubic pad connected to the lower end, a bowed elongated pectoral base bar having a pair of oppositely spaced terminals, a bar hinge pivotally connecting the base bar to an elongated sternal bar, said sternal bar connected to the upper end of the upright, said bar hinge having an axis of pivoting substantially perpendicular to the length of the upright, said base bar being generally perpendicular to the length of the upright, the improvement comprising; a pectoral pad bar releaseably connected to each of the terminals of the pectoral base bar, each of the pectoral pad bars being elongated, each of the pectoral pad bars having one end connected to the pectoral base bar, a pectoral pad hinge connected to the other end of each of the pectoral pad bars, and a pectoral pad connected to each of the pectoral pad hinges, each of the pectoral pad hinges having an axis of pivoting substantially parallel to the length of the upright, each pectoral pad having a domed resilient outer face plate having its central portion extending away from its respective hinge, and a resilient foam padding mounted on the side of the outer face plate away from the hinge.

* * * * *